(12) United States Patent
Iwata et al.

(10) Patent No.: US 6,386,091 B2
(45) Date of Patent: May 14, 2002

(54) CONTINUOUS PROCESSING APPARATUS

(75) Inventors: Hitoshi Iwata; Takaaki Shimizu; Katsuyuki Iwahata, all of Higashi-Osaka (JP)

(73) Assignee: House Foods Corporation, Osaka (JP)

(*) Notice: Subject to any disclaimer, the term of this patent is extended or adjusted under 35 U.S.C. 154(b) by 0 days.

(21) Appl. No.: 09/840,310

(22) Filed: Apr. 24, 2001

Related U.S. Application Data

(63) Continuation of application No. PCT/JP00/05628, filed on Aug. 23, 2000.

(30) Foreign Application Priority Data

Aug. 25, 1999 (JP) .............................. 11-237810

(51) Int. Cl.$^7$ .............................. A23L 1/00; A23L 1/10; A23L 1/182

(52) U.S. Cl. .............................. 99/330; 99/352; 99/359; 99/360; 99/367; 99/417; 99/443 C; 99/473; 99/483; 99/516

(58) Field of Search ................... 99/326–331, 352–356, 99/359–362, 367–371, 403–417, 443 R, 443 C, 447–450, 467–473, 483, 516, 536; 53/451, 551, 552, 471, 474, 430, 461; 422/21–23, 39; 426/506, 507, 115, 118, 124, 316, 326, 395, 410, 510, 521, 523, 511; 219/401, 400; 126/21 A

(56) References Cited

U.S. PATENT DOCUMENTS

| | | | | |
|---|---|---|---|---|
| 4,059,919 A | * | 11/1977 | Green | 99/356 |
| 4,571,341 A | * | 2/1986 | Sugimura | 99/404 X |
| 4,607,495 A | * | 8/1986 | Fujimoto et al. | 99/537 X |
| 4,649,055 A | * | 3/1987 | Kohlwey | 426/521 X |
| 4,677,907 A | * | 7/1987 | Weibye | 99/483 |
| 4,866,232 A | * | 9/1989 | Stone | 99/403 X |
| 4,882,188 A | * | 11/1989 | Sawada et al. | 99/470 X |
| 5,069,923 A | * | 12/1991 | Hubbard et al. | 99/356 X |
| 5,130,153 A | * | 7/1992 | McIlroy et al. | 99/330 X |
| 5,241,149 A | * | 8/1993 | Watanabe et al. | 426/410 X |
| 5,355,777 A | * | 10/1994 | Chen et al. | 99/403 X |
| 5,370,042 A | * | 12/1994 | Tolchin et al. | 99/407 X |
| 5,587,194 A | * | 12/1996 | Nakatani et al. | 426/521 |

* cited by examiner

*Primary Examiner*—Timothy F. Simone
(74) *Attorney, Agent, or Firm*—Jacobson Holman, PLLC

(57) ABSTRACT

A continuous processing apparatus comprises a tubular assembly that has a carrying path of a constant spatial cross sectional area throughout it and a pressure control unit in the carrying path, a retainer that is provided with throttle pieces of an area slightly smaller than the spatial cross sectional area so as to create labyrinth seal at least one of the upstream and downstream locations from the pressure control unit of the tubular assembly along its carrying path, and a retainer carrying device placed in the tubular assembly for carrying the retainer.

12 Claims, 7 Drawing Sheets

CONTINUOUS PROCESSING APPARATUS

This is a Continuation Application of PCT International Application No. PCT/JP00/05628, filed Aug. 23, 2000.

FIELD OF THE INVENTION

The present invention relates to a continuous processing apparatus, and more particularly, it relates to a continuous processing apparatus that has a specific section provided with labyrinth seal to retain pressure controlled conditions, so that sterilizing procedure and hot cooking procedure are sequentially carried out under pressurized or pressure reduced condition.

PRIOR ART

Technologies where pressure control procedure requires pressurizing include alunitization (sealing) on aluminum products, resin curing on reinforced plastic, polymer impregnated reinforcement manufacturing (Japanese Examined Patent Publication SHO58-18532), synthetic foam resin manufacturing (Japanese Examined Patent Publication SHO 60-55283), sterilization of medical equipment and food ingredients, and so forth.

An apparatus that carries out the pressurizing in a manner of batch processing is designed so as to perform sequential processing procedures under atmospheric pressure, pressurized condition for the purpose of sterilizing, pressure reduced condition, and atmospheric pressure regained condition in a single pressurizing and processing apparatus, and, it is disclosed, for example, in an official gazette of Japanese Unexamined Patent Publication HEI 9-84567. Although the HEI 9-84567 discloses a pressure and heat sterilizing apparatus of a batch processing type, such an apparatus must be provided with a sterilizing room having a control mechanism to repeat procedures of pressurizing a processing chamber, processing raw/semi-processed materials, and reducing pressure in the processing chamber, and a tremendous cost of equipment investment is required to enhance throughput. There also arise problems that this requires larger-scale plant and equipment as well as more complicated control system. Moreover, even after solid food contained in retainers are sterilized, till the solid food is emptied out of the retainers into final product containers, the retainers are left standing by, and the sterilized solid food in those retainers may be contaminated with germs and viruses.

In such an apparatus that carries out pressurizing procedures continuously, a pressurizing apparatus must be led, in an upstream location therefrom, by a pressure regulation room to selectively adjust pressure from atmospheric pressure level up to pressurized level in order to carry materials to be processed in the tightly sealed pressurizing apparatus. Also, the pressurizing apparatus must be trailed, in a downstream location therefrom, by another pressure regulation room to selectively adjust pressure from pressurized level down to atmospheric pressure level in order to carry the processed materials out of the pressurizing apparatus. For instance, an official gazette of Japanese Unexamined Patent Publication HEI 7-67595 discloses an apparatus that continuously sterilizes food ingredients contained in retainers. Specifically, in the disclosed design, a food ingredient supply unit, a linear tubular heater, a linear tubular cooler, and a dispensing unit are arranged in this order while the linear tubular heater and cooler have their respective inlets and outlets provided with dual tight seal gates or valves to sequentially open and close the gates, so that the unprocessed and processed materials are supplied to and ejected from the linear tubular heater and cooler, respectively, with the pressure kept unchanged.

In such an apparatus, each time the unprocessed and processed materials are carried in and out of the linear tubular heater and cooler, the dual tight seal gates must be alternately opened and closed, and thus, there arise problems of complicated operability and degraded durability of the apparatus.

A continuous rice steaming apparatus is disclosed in Japanese Unexamined Patent Publication SHO 52-64470, where pressurizing procedures are continuously carried out without providing tight seal gates. This apparatus has endless, continuous conveyer belt, and a plurality of continuous housings with partitioning panels located at constant intervals in a conveyer belt running direction and with side panels located along sides of the conveyer belt. Part of a running path of the conveyer belt passes through a steam heating chamber, and the steam heating chamber has an conveyer belt inlet and outlet where the partitioning panels serve as gates to define minute clearances.

The continuous rice steaming apparatus has its conveyer belt complicated in configuration to cause difficulty in washing it. The conveyer belt is required to be considerably long to result in the continuous rice steaming apparatus becoming larger in size, and additionally, the conveyer belt may be unavoidably flexed because of thermal expansion to cause difficulty in operation control and maintenance. Furthermore, a drive unit of the conveyer belt must be provided in the outside of the steam heating chamber, and thus, it is difficult to keep the continuous rice steaming apparatus sterilized. Moreover, since the housings are contiguous, materials, such as cooked rice, that have already been processed with pressure and heat in the housings are difficult to be emptied out of each of the housings into a final product container, and this results in applicable food materials being limited to some range.

On the other hand, technologies where pressure control procedure requires pressure-reducing include swelling chocolate manufacturing of a batch process type as disclosed in an official gazette of Japanese Unexamined Patent Publication HEI 6-191515, and a pressure-reducing fryer that enables continuous processing as disclosed in an official gazette of Japanese Unexamined Patent Publication HEI 6-7255. Such pressure reducing apparatus must also be provided with a sterilizing room having a control mechanism to repeat procedures of reducing pressure in a processing chamber, processing raw/semi-processed materials, and pressurizing in the processing chamber, and a tremendous cost of equipment investment is required to enhance throughput. There also arise problems that this requires larger-scale plant and equipment as well as more complicated control system.

In such an apparatus that carries out pressure-reducing procedures continuously, a pressure reducing apparatus must be led, in an upstream location therefrom, by a pressure regulation room to selectively adjust pressure from atmospheric pressure level down to pressure reduced level in order to carry raw/semi-processed materials in the pressure reducing apparatus. Also, the pressure reducing apparatus must be trailed, in a downstream location therefrom, by another pressure regulation room to selectively adjust pressure from pressure reduced level up to atmospheric pressure level in order to carry the processed materials out of the pressure reducing and processing apparatus. The above mentioned dual tight seal gates must also be alternately opened and closed, and this results in durability of the apparatus being degraded.

OBJECTS OF THE INVENTION

Accordingly, the present invention is directed to overcome the disadvantages as stated above in the prior art pressurizing apparatus and pressure reducing apparatus, and it is an object of the present invention to provide a continuous processing apparatus in which a tubular assembly creates labyrinth seal to define a pressure controlled processing unit and to define inlet and outlet to keep pressure controlled in the unit while raw/semi-processed materials are being carried in and out therethrough, so as to considerably simplify an arrangement of a pressure processing apparatus, facilitate to sterilize the apparatus, retain the sterilized conditions well, omit pressurizing and pressure reducing procedures in carrying raw/semi-processed materials in and out of the processing apparatus, and quickly activate a subsequent procedure on the processed materials.

It is another object of the present invention to provide a continuous processing apparatus in which a pressure processing unit has a very small volume of idle space so as to reduce loss of steam and thermal energy required for processing for the purpose of energy saving, and so as to obtain even conditions of and stable controls over pressure and temperature.

It is still another object of the present invention to provide a continuous processing apparatus in which the processed materials can be effectively and easily emptied into final product containers with extremely reduced residual materials, and a delivery route can be arbitrarily determined to down-size the apparatus.

In general, labyrinth seal is defined as seal that is created by an arrangement where a plurality of throttle pieces are provided to define narrow flow paths, and the narrow flow paths and large spaces are alternately located in a specified section to permit pressure therein to be enhanced or reduced stepwise, and to permit the specified section to substantially be shielded against pressure variation, and more specifically, it is defined as mechanism in which extremely narrow throttle flow paths are provided at intervals between the inner walls of a carry-in and carry-out paths in a pressure controlled processing room and a carrying unit of raw/semi-processed materials, so as to substantially prevent leak of fluid.

MEANS TO OVERCOME PRIOR ART DISADVANTAGES

The present invention provides a continuous processing apparatus that comprises a tubular assembly having a carrying path of a constant spatial cross sectional area throughout it and a pressure control unit in the carrying path, a retainer that is provided with throttle pieces of an area slightly smaller than the spatial cross sectional area so as to create labyrinth seal at least one of the upstream and downstream locations from the pressure control unit of the tubular assembly along its carrying path, and a retainer carrying device placed in the tubular assembly for carrying the retainer.

Preferred embodiments of the present invention will be described hereinafter.

A preferred embodiment of the present invention is characterized in that the tubular assembly has a pressure control unit trailed, in a downstream location therefrom, by a container supply unit which supplies a sterilized container to engage an opening of the sterilized container with an opening of the retainer. With such an arrangement, the processed materials that have been heated and sterilized can be emptied into the sterilized container without aids of shoot, for example, and thus, the prior art disadvantage that the residuals of the processed materials in the shoot may cause contamination with germs and viruses can be eliminated.

A preferred embodiment of the present invention is characterized in that the tubular assembly has the pressure control unit led, in an upstream location therefrom, by a preliminary heating unit. With such an arrangement, the raw/semi-processed materials can be quickly heated and sterilized so as to effectively prevent deterioration and deformation of the materials.

A preferred embodiment of the present invention is characterized in that the tubular assembly has the container supply unit trailed, in a downstream location therefrom, by a retainer/container turning unit that rolls over the retainer united with the container. With such an arrangement, the raw/semi-processed materials can be effectively emptied into the container without spill nor without deformation due to impact and shock.

A preferred embodiment of the present invention is characterized in that the retainer/container turning unit is trailed, in a downstream location therefrom, by a container dispensing unit, a sterilized top supply unit, and a top tight seal unit. With such an arrangement, the processed materials can be effectively prevented from being contaminated.

A preferred embodiment of the present invention is characterized in that the retainer/container turning unit has its downstream portion connected to an upstream portion of the tubular assembly via a retainer wash unit. With such an arrangement, the retainer can effectively be carried repeatedly and used efficiently. A preferred embodiment of the present invention is characterized in that the retainer carrying device utilizes magnetic force to carry the retainer. With such an arrangement, the interior of the tubular assembly and the retainer can be extremely simplified in their respective configuration, and hence, some procedure like washing can be carried out quickly and assuredly, and the apparatus can supremely effectively keep itself sterilized. Additionally, a required cost of plant and equipment can be effectively reduced.

A preferred embodiment of the present invention is characterized in that the retainer carrying device may utilizes carrying gears to carry the retainer within and through the tubular assembly. With such an arrangement, the retainer can effectively be carried assuredly with reduced carrying force.

A preferred embodiment of the present invention is characterized in that the tubular assembly is circularly shaped in cross section, and the throttle pieces are also circularly shaped in contour. With such a configuration, narrow clearances can be created evenly and extremely accurately between the tubular assembly and the throttle pieces, and the even clearances can be ensured even when the tubular assembly and the throttle pieces are thermally expanded, so as to ensure that the clearances effectively produce labyrinth seal effects.

A preferred embodiment of the present invention is characterized in that the tubular assembly has a plurality of steam supply nozzles. With such an arrangement, the tubular assembly can be divided into a plurality of subsections under varied heating conditions from one another, so as to carry out the heating stepwise depending upon types and natures of the materials to be processed.

Alternatively, the pressure control unit is led, in an upstream location therefrom, by a preliminary heat processing unit filled with steam ambience with the labyrinth seals intervening therebetween. With such an arrangement, steam leaked from the labyrinth seals can be effectively used to carry out some procedures like preliminary heating.

An alternative embodiment is characterized in that the pressure control unit is trailed, in a downstream location therefrom, by a steam atmosphere processing room with the labyrinth seals intervening therebetween. With such an arrangement, steam leaked from the labyrinth seals can be effectively used to carry out some procedures like sterilized packing.

DETAILED DESCRIPTION OF THE INVENTION

Figure 1:
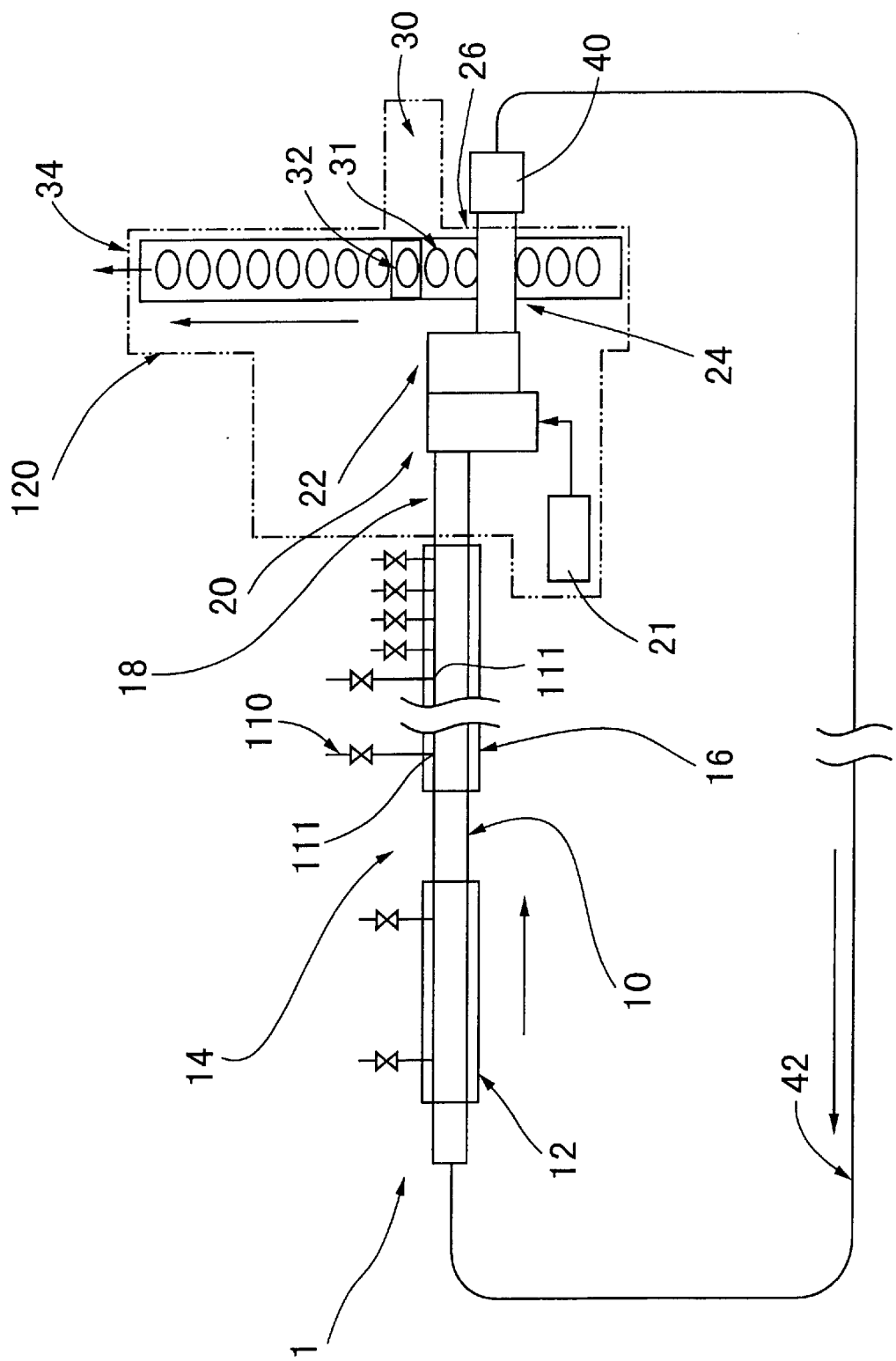
FIG. 1 is a diagram generally showing a continuous processing apparatus of a first preferred embodiment according to the present invention.
Figure 4:
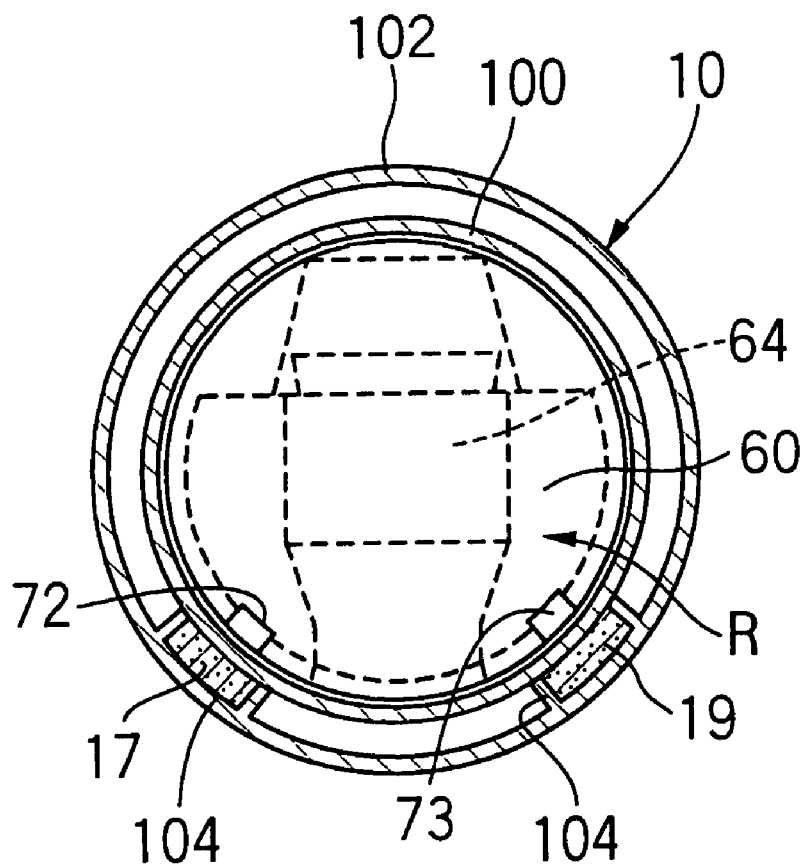
FIG. 4 is a vertical cross-sectional view taken along the line V—V of FIG. 3.

A continuous pressurizing apparatus of a first preferred embodiment according to the present invention, namely, a thermal food sterilizing apparatus 1, includes a tubular assembly 10 that is linear in shape and has an inner cylindrical cavity of a constant cross-sectional area defined throughout its length, and the tubular assembly is comprised of a preparatory heating unit 12, a labyrinth seal pressurizing unit 14, a pressure controlled processing chamber 16, and a labyrinth seal pressure reducing unit 18 which are all arranged in this order from the upstream along a processing line in a transfer direction of retainers R, as depicted in FIG. 1. The tubular assembly 10 has, as shown in FIG. 4, retainer transfer electromagnetic bands 17 and 19 as mentioned hereinafter, on the opposite sides thereof.

Figure 5:
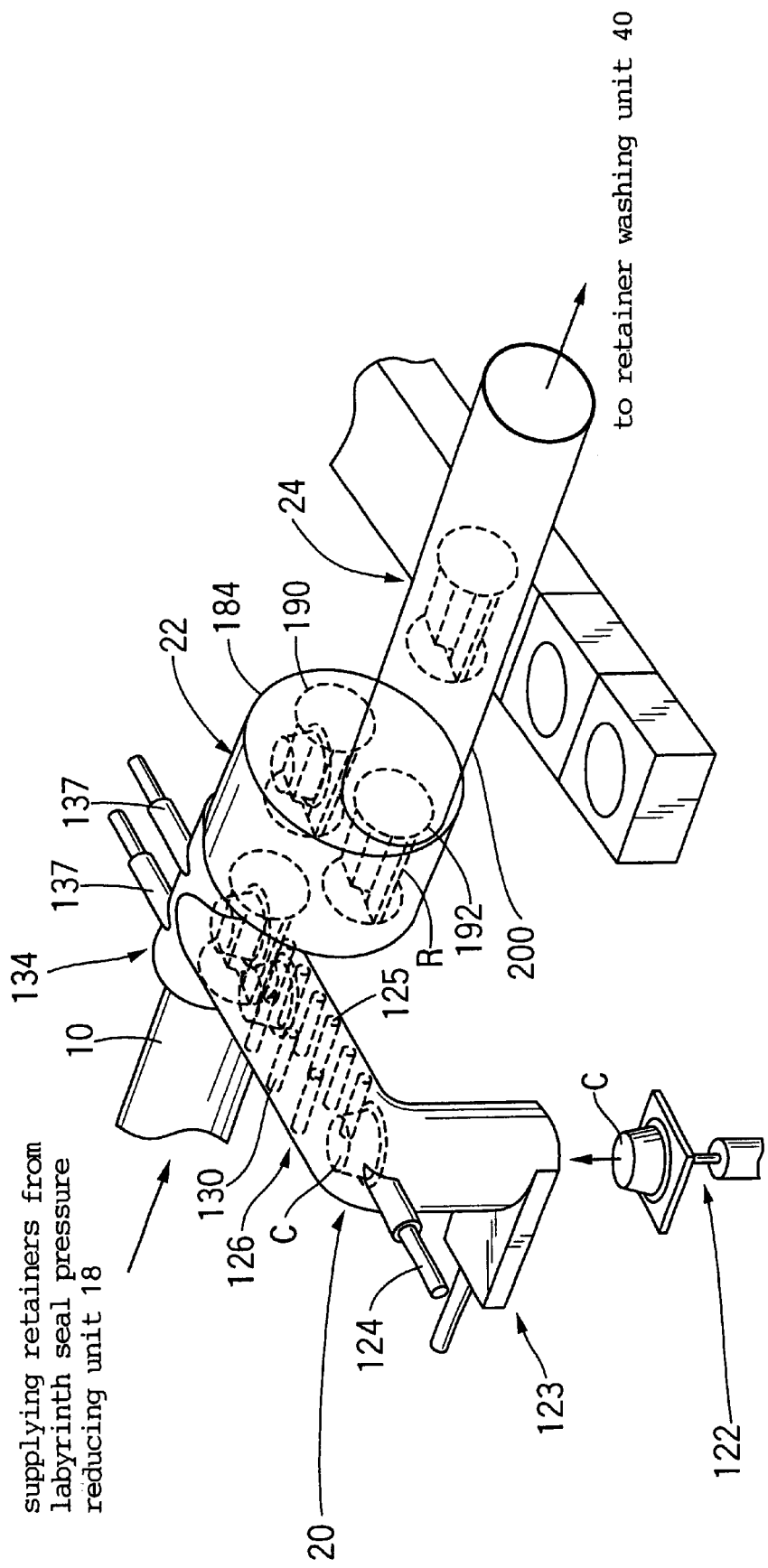
FIG. 5 is a perspective view showing a container supply unit and a turning unit, and their nearby regions of the first preferred embodiment according to the present invention.

As depicted in FIGS. 1 and 5, the labyrinth seal pressure reducing unit 18 is, in downstream locations therefrom, followed by a container supply unit 20 that supplies sterilized containers C to cap the retainers R, a turning unit 22 that rolls over the retainers R capped and united with the containers C to load the containers C with sterilized solid food ingredients such as base material and cooked rice that have been contained in the retainers R, a container dispensing unit 24 that dispenses the containers loaded with the solid food, and a retainer ejecting unit 26 that ejects the retainers R rolled over and evacuated. The container supply unit 20 is connected to a sterilizing apparatus (not shown) that receives the containers C shaped and transferred from a container molding apparatus 21 or somewhere else to sterilize them.

As depicted in FIG. 1, the container dispensing unit 24 is trailed, in downstream locations therefrom, by a gas replacement unit 31 that turns the air in the containers C to inert gas such as nitrogen gas, a top supply apparatus 30 which supplies sterilized tops L to the containers C, a top seal unit 32 that tightly fasten the tops L to the containers C, and a final product dispensing unit 34, as depicted in FIG. 1. As required, a liquid supply apparatus (not shown) may be placed between the container dispensing unit 24 and the gas replacement unit 31 to inject sterilized liquid.

Further, the retainer ejecting unit 26 is, in downstream locations therefrom, trailed by a retainer wash unit 40, and a retainer feedback line 42 that delivers the retainers R washed in the previous stage, to the preparatory heating unit 12, in the described order.

Figure 2:
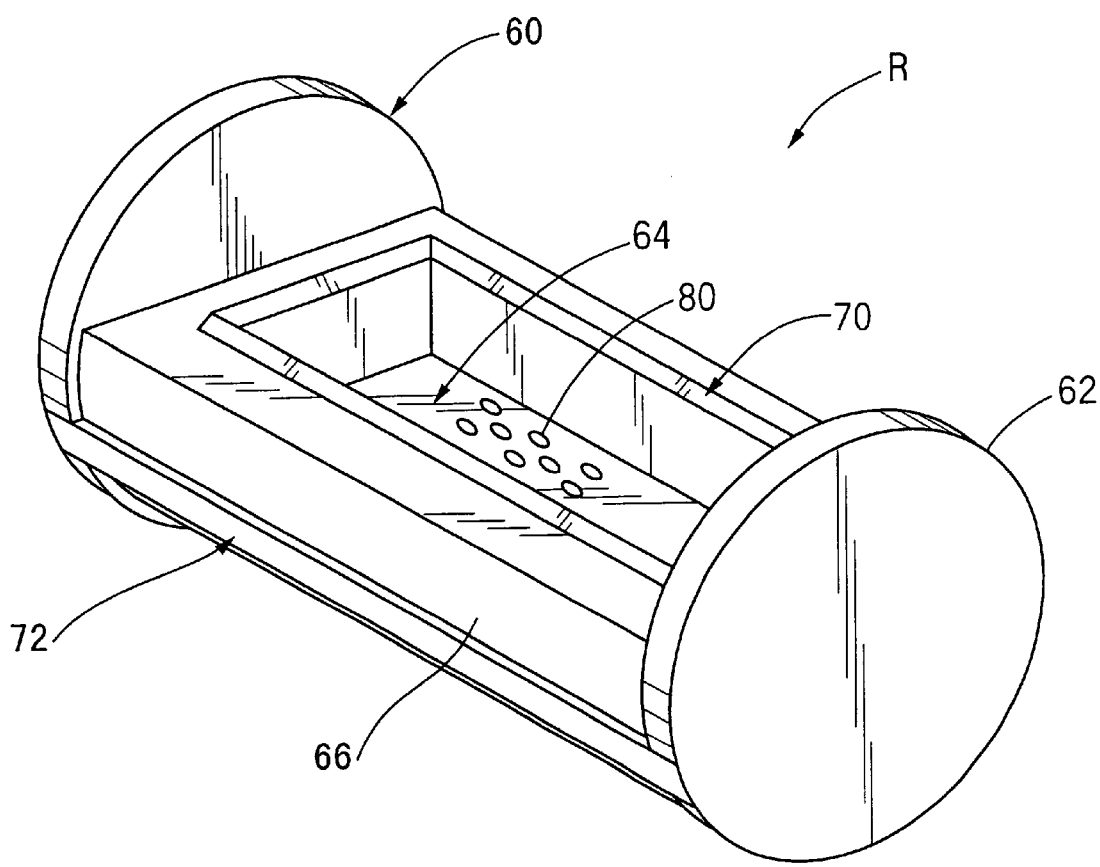
FIG. 2 is a perspective view of a retainer of the first preferred embodiment according to the present invention.

Each of the retainers R, as shown in FIG. 2, has its outermost surface circularly shaped, and it is provided with circular labyrinth seal throttle pieces 60 and 62 at the fore and after opposite ends of its length in its delivery direction to create labyrinth seals and is also provided with a box-shaped housing 66 to contain food ingredients. Inside the housing 66, food container 64 is defined with punched plate 80 at its bottom, and a container engagement portion 70 is formed, surrounding an upper opening of the housing 66, to engage with each of the containers C. To the opposite sides of the housing 66, carrying magnets 72 and 73 are horizontally attached, with N and S poles of the permanent magnets being alternately positioned with each other at specified pitches.

The housing 66 of the retainer R is left open below the punched plate 80.

Figure 3:
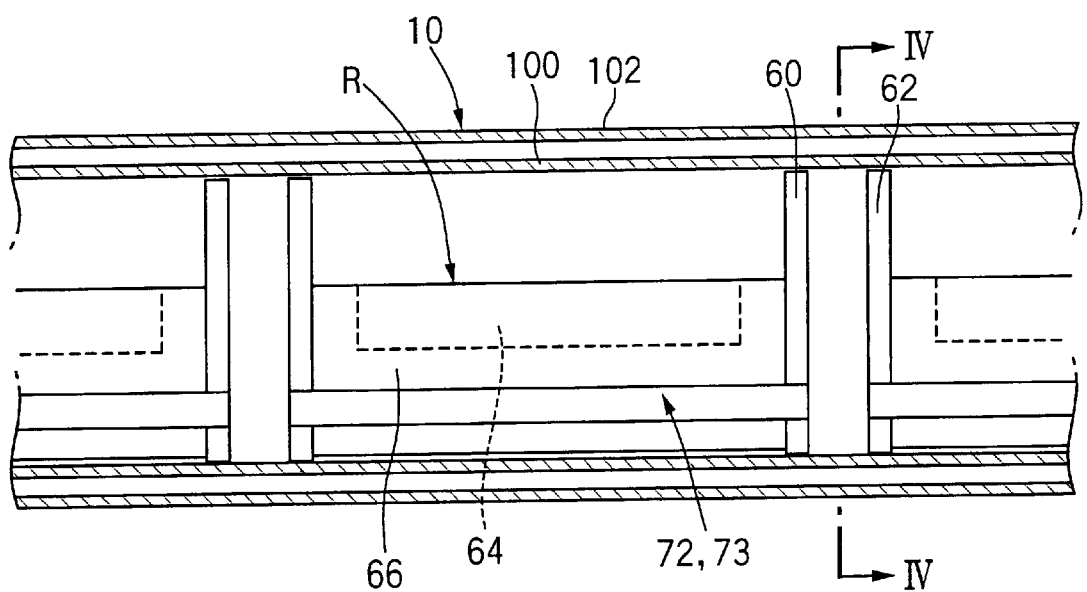
FIG. 3 is a vertical cross-sectional view showing a tubular assembly along its transfer direction of the first preferred embodiment according to the present invention.

The tubular assembly 10 is, as illustrated in FIGS. 3 and 4, configured in dual-shell arrangement, i.e., in jacketed shell arrangement, comprised of an inner tubular member 100 and an outer tubular member 102, as desired. Between the inner and outer tubular members 100 and 102, there are defined sectioned chambers 104 extending 45° below the common horizontal radii of those members along both of their respective left and right opposite sides in the retainer delivery direction, and the retainer carrying electromagnetic bands 17 and 19 are positioned in the sectioned chambers. The retainer carrying electromagnetic bands 17 and 19 are cooperative with the carrying magnets 72 and 73 to carry and deliver the retainer R. A conveyer may be substituted, which includes permanent magnets with their N and S poles alternately positioned with each other, to carry and deliver the retainer R.

Referring to FIG. 1 again, the preliminary heating unit 12 supplies saturated steam to the tubular assembly 10 to preliminary heat raw/semi-processed food ingredients for subsequent processing.

The labyrinth seal heating unit 14 and the labyrinth seal pressure reducing unit 18 create labyrinth seal by defining clearances of about 0.3 mm between the inner tubular member 100 of the tubular assembly 10 and the labyrinth seal throttling pieces 60 and 62 of the retainer R. Consequently, pressure level in the labyrinth seal pressurizing unit 14 varies from atmospheric pressure to higher pressure as it is measured in positions progressively downstream in the retainer delivery direction, so that the pressure controlled processing chamber 16 keeps its pressurizing conditions unchanged. The labyrinth seal pressure reducing unit 18, while creating labyrinth seal as in the labyrinth seal pressurizing unit 14, reduces pressure level to atmospheric pressure as it is measured in positions progressively downstream so that the pressure controlled processing chamber 16 keeps its pressurizing conditions unchanged.

The pressure controlled processing chamber 16 supplies pressurizing steam from an upper portion of the tubular assembly 10 via a link tube 110, as depicted in FIG. 1, to pressurize and thermally process the food ingredients contained in the retainer R. The link tube 110 is comprised of a plurality of nozzles 111 located along a retainer delivery path, and conditions of pressurizing steam injected from the nozzles 111 can be varied to attain stepwize pressurizing and thermal processing suitable to the food ingredients as desired.

Additionally, by virtue of the plurality of nozzles, subsections used for thermal processing can be arbitrarily selected depending upon materials to be processed, and thus, setting and controlling the conditions of thermal processing can be facilitated.

The container supply unit 20, turning unit 22, container dispensing unit 24, and retainer ejecting unit 26 are filled with steam ambience to keep the sterilized conditions, and since, as shown in FIG. 1, the whole section of these units are housed in a clean room 120, sterilized food ingredients, the retainers R, the tops, and the like stored in this section is prevented from contamination with germs and viruses.

The container supply unit 20 uses a container supply cylinder apparatus 122, as shown in FIG. 5, to lift the container C shaped by the container molding apparatus 21 shown in FIG. 1, and it also uses a gate valve 123 which opens to supply the container C to a container carrying and sterilizing apparatus 126. The container carrying and sterilizing apparatus 126 has its inside sterilized by UV lamp 130 and causes a container thrusting apparatus 124 to horizontally thrust the container C received from the container supply cylinder apparatus 122, so that the container C is delivered on container carrying rollers 125 and engaged with the retainer R at the container engagement portions 70 by a container loading apparatus 134.

The container loading apparatus 134 has its suction device (not shown) lowered to be affixed to the bottom of the faced-down container C at several points by suction force. The container loading apparatus 134, after shifting the container C to a position where the container C can be engaged with the retainer R at the container engagement portion 70, lowers the container C and makes the suction device (not shown) release it.

Figure 6:
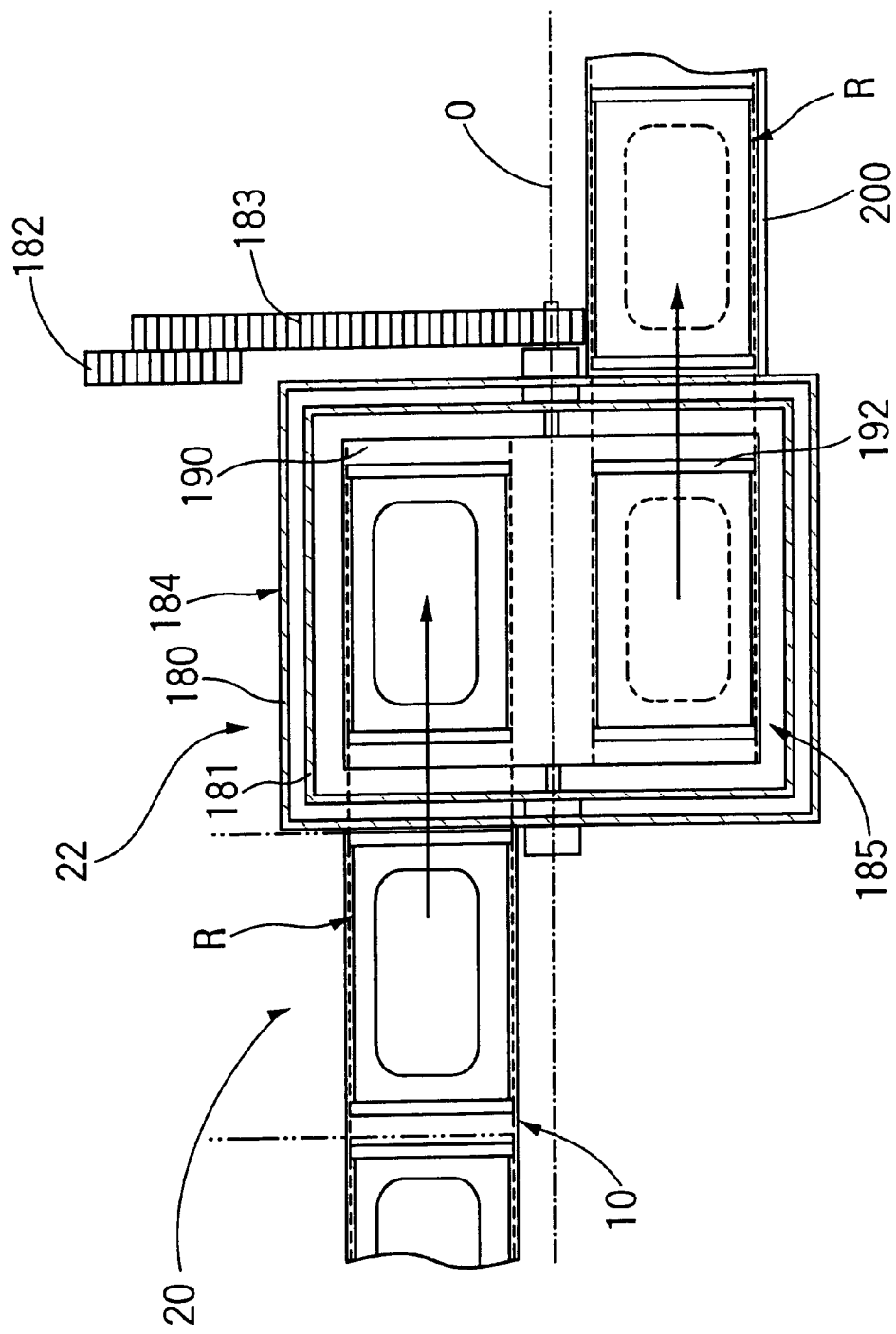
FIG. 6 is a horizontal cross-sectional view showing the turning unit of the first preferred embodiment according to the present invention.

The turning unit 22 includes a warming jacket 184, as shown in FIG. 6. The turning unit 22 keeps its inside sterilized. A turning drum 185 can be rolled over about a center axis 0 by gear 182, serving as a turning power source, and drive belt 183. The turning drum 185 comprises container/retainer housing spaces 190 and 192 that accommodate the retainers R united with the containers in symmetrical locations about the center axis 0. When both the container/retainer housing spaces 190 and 192 are located at the same height, one of them, i.e., the container/retainer housing space 190 is in an extended position from the tubular assembly 10 while the other, i.e., the container/retainer housing space 192 is in an upstream extended position from the container dispensing unit 24. The turning unit 22 tumbles the turning drum 135 by 180° about the center axis 0 to empty processed food ingredients in the retainer R into the container C.

The retainer R separated from the container C in the container dispensing apparatus 24 is washed in the retainer wash apparatus 40, as shown in FIG. 1. Then, the retainer R is delivered to the preliminary heating unit 12 via a retainer feedback line 230.

Figure 7:
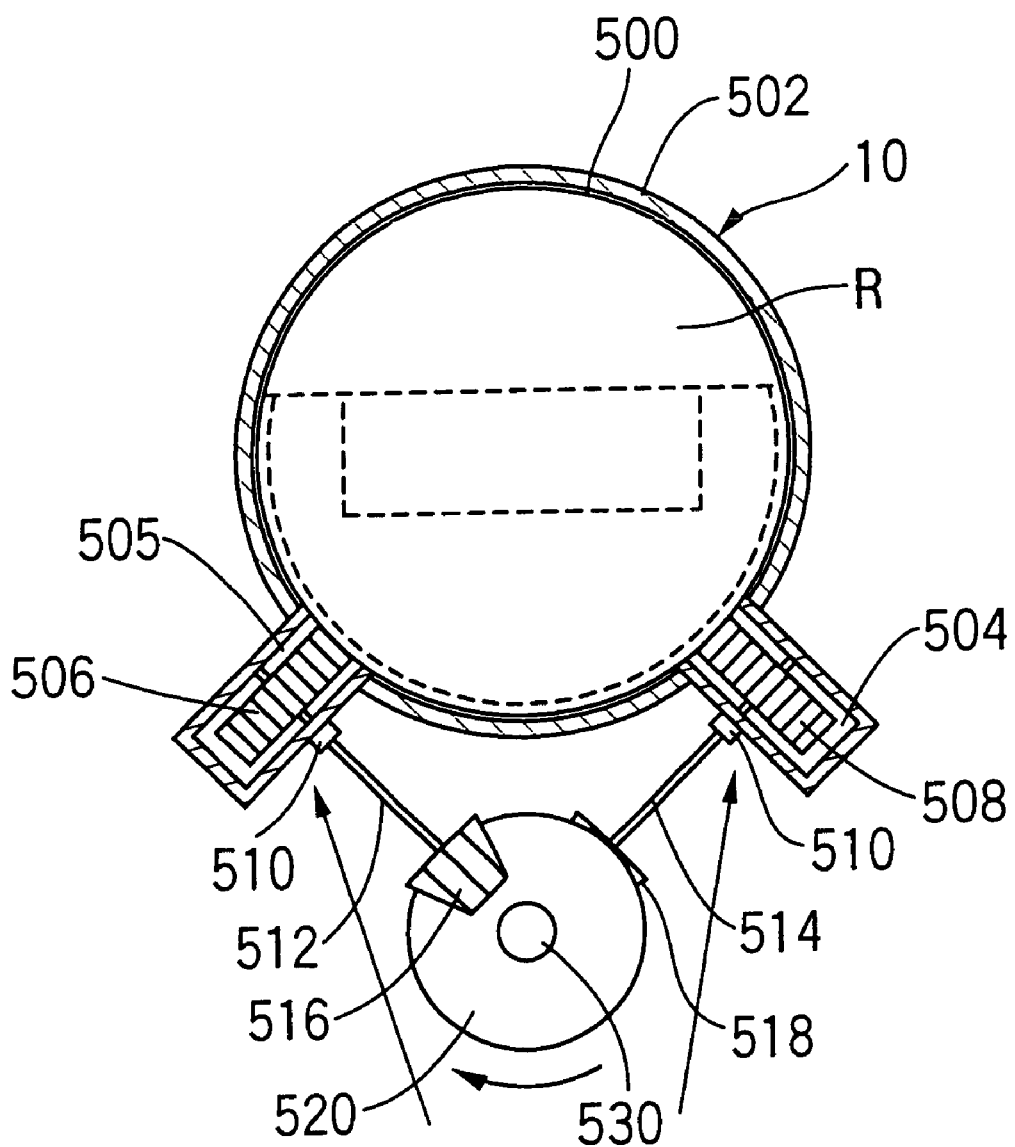
FIG. 7 is a combined horizontal and vertical cross-sectional view showing another continuous processing apparatus according to the present invention.

In an alternative embodiment of the present invention, corrugated panel may be substituted for the retainer carrying magnets as mentioned above, and in such an arrangement where a cam mechanism is used to carry the retainers R, as shown in FIG. 7, there are defined sectioned chambers 504 and 505 extending 45° below horizontal radii of the tubular assembly 10 along both the left and right opposite sides thereof in the retainer delivery direction, with pairs of retainer carrying gears 506 and 508 being positioned at intervals shorter than the retainer R in the sectioned chambers 504 and 505 in the delivery direction. The retainer carrying gears 506 and 508 are rotated by carrying shafts 512 and 514 extending through a sterilized pressure-durable seal bearing 510 into the sectioned chambers 504 and 505, conical cams 516 and 518 attached to the carrying shafts 512 and 514, a conical drive cam 520 engaged with the conical cams 516 and 518, and a drive shaft 530 attached to the conical drive cam 520, so as to carry and deliver the retainers R.

EFFECTS OF THE INVENTION

In a continuous processing apparatus configured as mentioned above according to the present invention, since a tubular assembly create labyrinth seals to define a pressure controlled processing unit and raw/semi-processed material carry-in and carry-out units to retain pressure controlled conditions, its pressure processing device can be of very simple configuration, the apparatus can be sterilized easily and can retain its sterilized condition well, the apparatus requires no procedures of pressurizing nor pressure reducing in carrying raw/semi-processed materials in and out of it, and the apparatus allows succeeding procedures to be quickly activated to further process the processed materials.

Also, according to the present invention, the pressure processing unit has very small volume of idle space so as to reduce loss of steam and thermal energy required for processing for the purpose of energy saving, and so as to obtain even conditions and stable controls of pressure and temperature.

Further, according to the present invention, the processed materials can be effectively and easily emptied into final product containers with extremely reduced residual materials, and a delivery route can be arbitrarily determined to downsize the apparatus.

What is claimed is:

1. A continuous processing apparatus, comprising a tubular assembly that has a carrying path of a constant spatial cross sectional area throughout it and a pressure control unit in the carrying path, a retainer that is provided with throttle pieces of an area slightly smaller than the spatial cross sectional area so as to create labyrinth seal at least one of the upstream and downstream locations from the pressure control unit of the tubular assembly along its carrying path, and a retainer carrying device placed in the tubular assembly for carrying the retainer.

2. A continuous processing apparatus as defined in claim 1, wherein the tubular assembly comprises a container supply unit that is located in a downstream position from the pressure control unit for supplying a sterilized container to unite the retainer with the sterilized container by engaging their respective openings with each other.

3. A continuous processing apparatus as defined in claim 1, where the tubular assembly comprises a preliminary heating unit that is located in an upstream position from the pressure control unit.

4. A continuous processing apparatus as defined in claim 2, wherein the tubular assembly comprises a retainer/container turning unit that is located in a downstream position from the container supply unit to roll over the retainer united with the container.

5. A continuous processing apparatus as defined in claim 2, wherein the retainer/container turning unit is trailed, in a downstream location therefrom, by a container dispensing unit, a sterilized top supply unit, and a top sealing unit.

6. A continuous processing apparatus as defined in claim 2, wherein the retainer/container turning unit has its downstream end connected to an upstream end of the tubular assembly with the retainer wash unit intervening therebetween.

7. A continuous processing apparatus as defined in claim 1, wherein the retainer carrying device utilizes magnetic force to carry the retainer.

8. A continuous processing apparatus as defined in claim 1, wherein the retainer carrying device utilizes gears to carry the retainer within and through the tubular assembly.

9. A continuous processing apparatus as defined in claim 1, wherein the tubular assembly is circularly shaped in cross section, and the throttle pieces are circularly shaped in contour.

10. A continuous processing apparatus as defined in claim 1, wherein the tubular assembly comprises a plurality of steam supply nozzles.

11. A continuous processing apparatus as defined in claim 3, wherein the pressure control unit is led, in an upstream location therefrom, by a preliminary heating unit filled with steam ambience, with the labyrinth seal intervening therebetween.

12. A continuous processing apparatus as defined in claim 1, wherein the pressure control unit is trailed, in a downstream location therefrom, by a steam ambience processing chamber with the labyrinth seal intervening therebetween.

* * * * *